United States Patent [19]

Schlechtriemen et al.

[11] Patent Number: 4,710,848
[45] Date of Patent: Dec. 1, 1987

[54] SOLID STATE CELL

[75] Inventors: Gerhard-Ludwig Schlechtriemen, Lübeck; Gerhard Hötzel; Werner Weppner, both of Stuttgart, all of Fed. Rep. of Germany

[73] Assignee: Max-Planck-Gesellschaft zur Forderung der Wissenschaften e.V., Fed. Rep. of Germany

[21] Appl. No.: 898,904

[22] Filed: Aug. 21, 1986

[30] Foreign Application Priority Data

Aug. 16, 1985 [DE] Fed. Rep. of Germany ....... 3529335

[51] Int. Cl.$^4$ .................. H01G 7/00; G01N 7/10; G01N 31/00
[52] U.S. Cl. ........................ 361/280; 73/23; 422/98
[58] Field of Search ............ 73/23, 26; 250/281; 324/464; 422/90, 94, 98; 361/280, 433

[56] References Cited

U.S. PATENT DOCUMENTS

| 2,930,015 | 3/1960 | Blumer | 73/26 X |
| 3,658,479 | 4/1972 | Heijne et al. | 422/98 |
| 4,187,486 | 2/1980 | Takahashi et al. | 422/98 X |
| 4,198,850 | 4/1980 | Firth et al. | 73/23 |
| 4,313,338 | 2/1982 | Abe et al. | 73/23 |

Primary Examiner—Donald A. Griffin
Attorney, Agent, or Firm—McGlew & Tuttle

[57] ABSTRACT

A solid state cell for measuring the activity of a component of a mixture by using a solid ionic conductor, which is in contact on one side with a reference phase and on the other side with a phase sensitive to the gas component to be determined, is to be improved in such a manner that its detection sensitivity and measuring stability are increased. For this purpose, the gas sensitive phase contains an addition of a substance that increases the electronic conductivity and does not chemically react with the components of the sensitive phase and the gas to be determined.

7 Claims, 1 Drawing Figure

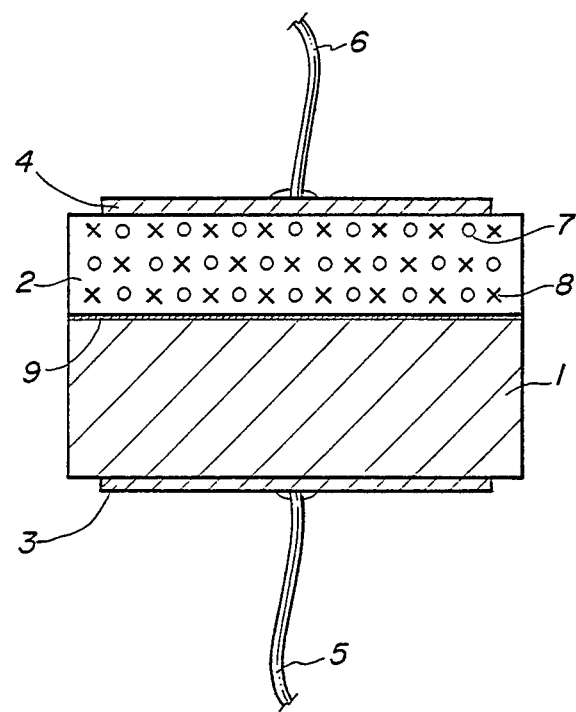

SOLID STATE CELL

FIELD AND BACKGROUND OF THE INVENTION

This invention relates in general to gas measuring devices and in particular to a new and useful solid state cell for measuring the activity of a component of a mixture.

The invention concerns a solid state cell for measuring the activity of a component in a mixture, especially for the determination of the partial pressure of a component of a gas mixture, with the use of a solid state ion conductor, which is in contact on one side with a reference phase and on the other side with a phase gas sensitive to the gas component to be determined, with lead electrodes provided at the reference phase and at the gas sensitive phase.

A solid state cell of this type has become known from German OS No. 29 26 172. In this solid state cell the ion conductor $LiAlCl_4$ is provided for measuring the partial pressure of chlorine, for exmaple that has acting as a gas sensitive phase an addition of $AlCl_3$ with which the solid state ion conductor is in phase equilibrium. The chlorine to be determined influences the gas sensitive phase and thereby the phase equilibrium between the gas sensitive phase and the ion conductor in such a manner that the activity of the mobile species is fixed at the boundary. An electromotive sorce (EMF) can be determined with the aid of one lead electrode, respectively, between the reference phase and the gas sensitive phase. But the observation was made that the adjustment of the EMF corresponding to the partial pressure of the gas to be determined frequently occurs only after a response time that is undesirably long for practical application.

It was also found that a stable measuring signal is established only after days, which fact does not allow the determination of quickly changing concentrations.

SUMMARY OF THE INVENTION

Thus, the present invention improves a solid state cell in such a manner that its response time, especially for low partial pressures of the gas component to be determined, is reduced at least so far that a stable measuring signal is established within minutes. This is achieved by an addition to the gas sensitive phase of a substance that increases the electronic conductivity and does not chemically react with the components of the sensitive phase and the gas to be determined.

Such an addition to the gas sensitive phase causes a catalytic activation of the component to be determined on the surface of the gas sensitive phase in such a manner that the subsequent coupling steps in the solid state cell to the ion conductor can take place with an accelerated rate to generate the EMF.

In a further practical realization of the invention, the substance may comprise a noble metal or an oxide of a noble metal, e.g. Pt or $PtO_x$.

The substance is prepared expediently as a mixed phase with the gas sensitive phase, that a mixed crystal structure can form, for example, by doping the gas sensitive phase consisting of AgCl with $CaCl_2$.

The addition of the substance to the gas sensitive phase can be performed in a particularly advantageous manner so that a mixture of both components, which changes continuously in its composition vertically to the interface, is formed as transition zone. The total impedance of the solid state cell is decreased by this graduation, which makes the determination of the EMF as zero-current-potential differenc between the lead electrodes easier with respect to measuring electronics. Such a transition zone may also be provided between the reference electrode and the ion conductor.

If the solid state cell has an additional separating layer between the ion conductor and the gas sensitive phase, this transition zone can be generated between the ion conductor and the separating layer as well as between the separating layer and the gas sensitive phase.

Accordingly, an object of the invention is to provide a solid state cell comprising a solid state ionic conductor, the cell being used for determining the activity or partial pressure, respectively, of a component in a gas mixture and which includes an electrical connection including electrodes arranged adjacent the ion conductor and also includes a gas sensitive phase which contains an additional substance in the gas mixture chamber for increasing the electronic conductivity which does not chemically react with the components of the sensitive phase and the gas to be determined.

A further object of the invention is to provide a solid state cell for measuring the activity of a component in a mixture which is simple in design, rugged in construction and economical to manufacture.

The various features of novelty which characterize the invention are pointed out with particularity in the claims annexed to and fomring a part of this disclosure. For a better understanding of the invention, its operating advantages and specific objects attained by its uses, refernece is made to the accompanying drawings and descriptive matter in which preferred embodiments of the invention are illustrated.

BRIEF DESCRIPTION OF THE DRAWINGS

In the Drawings

The only figure of the drawing is a sectional view of a solid state cell constructed in accordance with the invention.

DESCRIPTION OF THE PREFERRED EMBODIMENTS

Referring to the drawings in particular the invention embodied therein comprises a solid state cell which includes a solid ion conductor 1 arranged in contact with a gas sensitive phase 2. Electrical contacts including terminals 6 and 5 are connected to the cell by means of a lead electrode 3 at one side of the solid state ion conductor 1 and a lead electrode 4 on (the top) side of the gas sensitive phase 2.

The solid state cell shown in a sectional view in the figure comprises a solid ionic conductor 1, which is followed by a gas sensitive phase 2 as a measuring electrode. The ionic conductor 1 and the gas sensitive phase 2 are each connected with a respective lead electrode 3 and 4. The lead electrode 3 serves simultaneously as reference electrode. Conducting wires 5, 6 between which the corresponding measuring signal is generated and led to an evaluation unit (not shown in the drawing) are in contact with the lead electrodes 3 and 4.

In the gas sensitive phase 2, the basic material 7 is represented by circles, to which the substance 8, represented by x's, is added to increase the electronic conductivity.

The solid state cell in the example for the determination of the chlorine partial pressure consists of the solid state ion conductor 1 Ag-$\beta$-alumina. The basic material 7 of the gas sensitive phase 2 is AgCl and the additional substance 8 is platinum. The lead electrode consists of Ag, the lead electrode 4, of a Pt-gauze.

For the practical construction of a solid state cell, its outer surfaces with the exception of the gas sensitive phase, are enclosed in an inert capsulation (not shown in the drawing).

While specific embodiments of the invention have been shown and described in detail to illustrate the application of the principles of the invention, it will be understood that the invention may be embodied otherwise without departing from such principles.

What is claimed is:

1. A solid state cell for measuring the activity of a component of a mixture, especially for the determination of the partial pressure of a component of a gas mixture, comprising a solid state ion conductor, a reference phase in contact with one side of said ion conductor, in contact with the other side of said conductor, a phase sensitive for the gas component to be determined and with said gas sensitive phase lead electrodes provided at the reference phase and at the gas sensitive phase, respectively, and wherein said gas sensitive phase contains an addition of a substance that increases the electronic conductivity and does not chemically react with the components of said sensitive phase and the gas to be detected.

2. A solid state cell according to claim 1, wherein said substance is a noble metal added to said gas sensitive phase.

3. A solid state cell according to claim 1, wherein said substance is an oxide of a noble metal added to said gas sensitive phase.

4. A solid state cell according to claim 1, wherein said substance comprises a compound which with said gas sensitive phase forms a mixed crystal structure.

5. A solid state cell according to claim 1, wherein a mixture of both components, which continuously changes in its composition vertically to the interface, is formed as a transition zone at least between said solid ionic conductor and said gas sensitive phase.

6. A solid state cell according to claim 5, wherein said transition zone of a separating layer separating said solid state ion conductor from said gas sensitive phase is formed between said ion conductor and said separating layer as well as between said separating layer and said gas sensitive phase.

7. A solid state cell according to claim 1, wherein:
said solid state ion conductor is formed of Ag-$\beta$-alumina, said gas sensitive phase is formed of Ag-Cl and said additional substance that increases the electronic conductivity is platinum.

* * * * *